United States Patent [19]

Chambers

[11] Patent Number: 4,568,356

[45] Date of Patent: Feb. 4, 1986

[54] PROCESS FOR MAKING ANHYDROUS ALCOHOL FOR MIXING WITH GASOLINE TO MAKE GASOHOL MOTOR FUEL

[76] Inventor: John M. Chambers, 541 Tremont Ave., Westfield, N.J. 07090

[21] Appl. No.: 87,475

[22] Filed: Oct. 23, 1979

Related U.S. Application Data

[63] Continuation-in-part of Ser. No. 959,177, Nov. 9, 1978, abandoned.

[51] Int. Cl.[4] .............................................. C10L 1/02
[52] U.S. Cl. ......................................... 44/56; 44/77; 203/18; 203/19
[58] Field of Search ................... 44/56, 77; 203/18, 19

[56] References Cited

U.S. PATENT DOCUMENTS

| | | | |
|---|---|---|---|
| 1,372,465 | 3/1921 | Stevens | 44/56 |
| 1,412,233 | 4/1922 | Ellis | 44/56 |
| 1,490,520 | 4/1924 | Steffens | 203/19 |
| 1,676,735 | 7/1928 | Keyes | 203/19 |
| 1,699,355 | 1/1929 | Hammond | 44/56 |
| 1,744,503 | 1/1930 | Ricard | 203/19 |
| 1,744,504 | 1/1930 | Ricard | 203/19 |
| 1,860,554 | 5/1932 | Ricard et al. | 203/19 |
| 1,937,786 | 12/1933 | Ricard et al. | 203/19 |
| 1,940,699 | 12/1933 | Ricard et al. | 203/19 |
| 1,973,529 | 9/1934 | Guinot | 203/52 |
| 2,012,199 | 8/1935 | McElroy | 44/56 |
| 2,050,513 | 8/1936 | Van Peski et al. | 203/18 |
| 2,371,010 | 3/1945 | Wolfner | 44/56 |
| 2,591,672 | 4/1952 | Calleral | 44/56 |
| 3,575,818 | 4/1971 | West | 203/10 |
| 3,955,939 | 5/1976 | Sommer et al. | 44/53 |

*Primary Examiner*—Y. Harris-Smith
*Attorney, Agent, or Firm*—Morgan, Finnegan, Pine, Foley & Lee

[57] ABSTRACT

There is provided a process for making anhydrous alcohol denatured with gasoline for ready mixing with additional gasoline to make gasohol and in which aqueous alcohol is introduced into a dehydration drying column along with gasoline. The alcohol, containing gasoline, flows into the lower zone of the drying column and is recovered as a substantially non-aqueous alcohol-gasoline mixture which may be classified as completely denatured alcohol. The rising vapors of the gasoline entrain the water and some alcohol as azeotropes which flow out the top of the column as vapors which are condensed to form a gasoline layer which is returned to the column and a water layer which is removed. Additional water is also removed by decantation on the top several trays of the drying column where it is present as a separate liquid phase. The process also includes utilizing the heat to strip the alcohol from dilute fermented wort for the recovery and reconcentration of the alcohol in the water layers recycled from the drying column while preventing any gasoline from contaminating the fermented feed product and insuring that gasoline is present as a contaminent in all alcoholic streams. Provision is also made to insure that all light ends in the incoming gasoline are contained in the alcohol-gasoline product.

13 Claims, 4 Drawing Figures

PROCESS FOR MAKING ANHYDROUS ALCOHOL FOR MIXING WITH GASOLINE TO MAKE GASOHOL MOTOR FUEL

This application is a continuation-in-part of co-pending application Ser. No. 959,177, filed Nov. 9, 1978 now abandoned and entitled Process for Making Motor Fuel Containing Alcohol.

This invention relates to a process for making motor fuel. More particularly the invention relates to a process for making anhydrous alcohol containing sufficient gasoline for denaturing the alcohol so that it may be conveniently used for blending with gasoline to make gasohol.

BACKGROUND OF THE INVENTION

In recent years rapidly increased consumption of natural petroleum products, particularly gasoline, and the consequent diminution of natural petroleum reserves have become serious problems throughout the world. Conservation measures, as well as research for substitute fuels and other sources of energy, have become of paramount importance and a wide variety of programs have been under consideration and actually commenced in order to solve these fundamental problems. Among such programs are many which deal with motor fuels, including the search for new fuels, alteration of presently known fuels, improved fuel manufacturing processes, the development of new types of engines and, as well, efforts to make current engines more efficient while consuming less fuel.

The technology for altering presently known motor fuels has been known for some time. For example, the mixing of gasoline and alcohol and gasoline, alcohol and/or water to provide a suitable motor fuel for internal combustion engines has been known for many years. However, such fuels have heretofore never become widely commercially acceptable because of the ready availability of gasoline derived from natural petroleum at relatively acceptable prices. The dwindling supply of natural petroleum and increased prices of the same in recent times, however, have made such altered fuels more attractive.

Among such altered fuels one of the most suitable for use in internal combustion engines is gasoline containing alcohol. This is especially so since alcohol not only has good combustion properties but is also readily available from a wide variety of sources such as, for example, grains, as an industrial by-product, and also a product of waste materials. This is particularly true with respect to ethanol per se.

On the other hand, it is known that alcohol, and particularly ethanol, forms an azeotrope with water and cannot be completely separated from such water by simple distillation procedures. Commercial plants generally produce ethanol containing 6% to 7% water by weight which, when mixed with gasoline in the range of about 10% alcohol and 90% gasoline, forms two liquid phases.

Consequently, the usual procedure in making an alcohol-gasoline mixture is to first remove the water from commercially manufactured alcohol by using an entrainer and then mixing the dry alcohol with a suitable motor fuel such as gasoline, the combined product being generally referred to as gasohol. For example, a typical process system for making gasohol includes a dehydration drying column and a stripper or recovery column, employing benzene or other suitable material which forms a ternary azeotrope with aqueous alcohol as an entrainer to remove water from commercial alcohol, the anhydrous alcohol subsequently being mixed with gasoline to form gasohol. However, such a system is not only relatively complex but must also be carefully balanced with the entrainer in order to give an anhydrous alcohol as a bottoms product, as explained more fully hereinafter. Therefore, presently known systems and processes for making gasohol are disadvantageous for the reasons mentioned above and there exists a need for a process for making motor fuel containing alcohol which does not have the inherent disadvantages previously mentioned.

For the alcohol producer it is desirable to make a fuel product directly instead of making alcohol and then dehydrating it. In the United States of America the alcohol must be made under government supervision and present procedures call for a government agent to check the quantity of 190 proof or higher spirits produced and as well, to be present when a denaturant is added to the alcohol. Special denaturing formulas and regulations require that the alcohol may only be shipped in bond to another bonded premises where it is used to make vinegar, diethyl ether, protein extractant or the like, or that the alcohol be completely denatured under government supervision. Completely denatured formulations must be prepared under supervision and only then may the product be removed from the premises without restrictions. The two completely denatured formulations, Formula #18 and Formula #19, presently specified by BATF (Bureau Alcohol and Tax Formula) Regulations call for the addition of certain materials to every 100 gallons of spirit. For example, Formula #18 calls for the addition of 2.5 gal methylisobutyl ketone, 0.125 gallon pyronate and 1.0 gallon of gasoline or kerosene for every 100 gallons of spirit. On the other hand, Formula #19 calls for the addition of 4 gallons methylisobutyl ketone and 1 gallon of gasoline or kerosene. In view of the present Gasohol Programs in the United States, recent regulations provide that alcohol containing at least 10% gasoline will be classified as completely denatured and thus be permitted to be removed from a distillery without restriction.

It is, therefore, a primary object of this invention to provide an energy efficient process for the production of an anhydrous alcohol product containing 85% to 90% alcohol with the remainder being conventional service station non-leaded gasoline, such product being made directly from fermented stock without the possibility of withdrawing or recovering an uncontaminated alcohol from the system.

It is another object of the invention to provide such a process without the possibility of contaminating the distillery grains or other feed stock residue of fermentation with the gasoline used in the process.

It is still a further object of the invention to provide a process which provides a product which will classify as completely denatured and thus one which may be removed from the manufacturing premixes without restriction, thus obviating the necessity for denaturing of the product in the presence of the BATF agent.

It is still another object of the invention to provide a process for the direct production from fermented stock of an anhydrous alcohol product containing 85% to 90% by weight alcohol, the remainder being conventional non-leaded gasoline, such as may be readily obtained directly from automotive gasoline stations or bulk supply terminals as the residue.

A still further object of the invention is the provision of a process which encompasses an entire plant process to satisfactorily produce an alcohol for fuel from a fermented feed containing alcohol in the usual concentration of up to about 12 volume % alcohol.

Other objects of this invention will be readily apparent from the following description thereof which is to be taken in conjunction with the accompanying drawings.

THE DRAWINGS

In order to illustrate the present invention more fully, attention is directed to the accompanying drawings which are to be taken in conjunction with the following description and wherein:

FIG. 1 is a flow sheet showing diagrammatically a typical known process for making motor fuel containing alcohol in which water is separated from aqueous alcohol by the use of benzene as an entrainer and the anhydrous alcohol subsequently mixed with gasoline; and FIG. 2 is a flow sheet showing diagrammatically a system arrangement suitable for making motor fuel containing alcohol in accordance with the process of this invention and employing gasoline or a gasoline fraction as an entrainer and extractant.

BRIEF STATEMENT OF THE INVENTION

Figure 1:
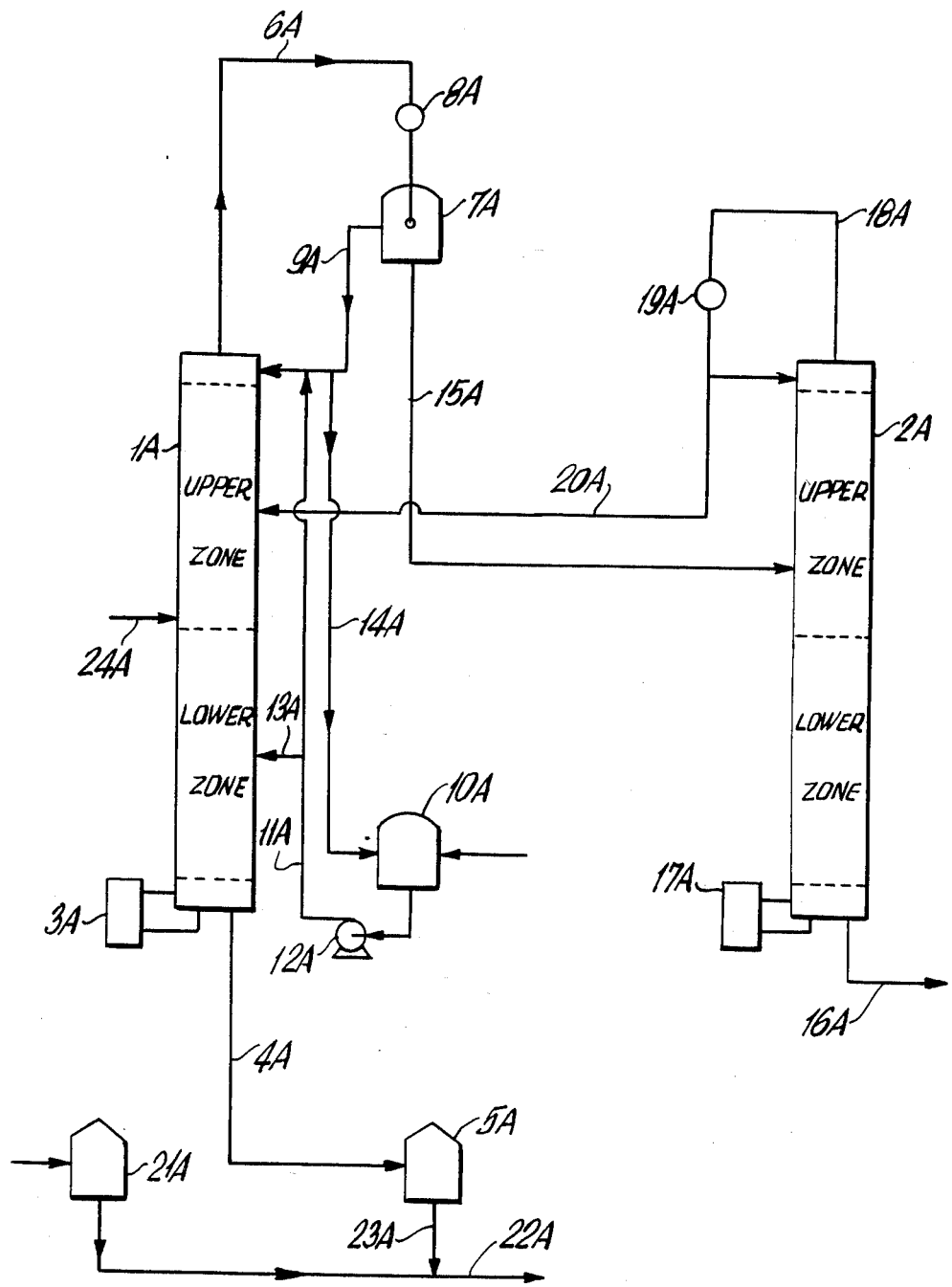

In accordance with the present invention there is provided a process for making motor fuel containing alcohol comprising introducing aqueous alcohol into a dehydration drying column having upper and lower zones and provided with a plurality of plates located one above the other in the column, vaporizing the aqueous alcohol and flowing the vapors upwardly in the upper zone while introducing a hydrocarbon in the form of gasoline or gasoline fraction into the upper zone at a point on the column above the point of introduction of the aqueous alcohol, flowing the gasoline downwardly into contact with the rising vapors and into the lower zone of the columm and entraining and extracting alcohol from the vapors with the gasoline, and, while taking as overhead vapors containing water, alcohol and gasoline from the upper zone of the column, and recovering a substantially non-aqueous mixture of gasoline and alcohol from the bottom or the lower zone of the column.

Expressed in other terms the present invention provides a process for making motor fuel containing alcohol comprising introducing aqueous alcohol into the upper zone of a dehydration drying column having upper and lower zones and provided with a plurality of plates located one above the other in the column while introducing a hydrocarbon in the form of gasoline or a gasoline fraction into the upper zone at a point on the column above the point of introduction of the aqueous alcohol and forming a ternary azeotropic mixture of the aqueous alcohol and the gasoline, subjecting the ternary azeotropic mixture to elevated temperature and vaporizing the aqueous alcohol, flowing the vapors upwardly in the upper zone while flowing the gasoline downwardly into contact with the rising vapors and into the lower zone of the column and entraining and extracting alcohol from the vapors, and, while taking as overhead vapors containing water, alcohol and gasoline from the upper zone of the column, and recovering a substantially non-aqueous mixture of gasoline and alcohol from the bottom or the lower zone of the dehydration drying column.

Since gasoline is a mixture of $C_6$–$C_{12}$ hydrocarbons with a considerable range of boiling points, that is, generally boiling points in a range of from about 80° F. (27° C.) to about 410° F. (210° C.), it, or a fraction, would not be indicated or considered as being a suitable or even possible entrainer for the elimination of water by azeotropic distillation. However, in the process of this invention where the desired product is an alcohol-gasoline mixture, the gasoline or a fraction thereof is used as an entrainer and extractant which is added at the top of the drying column to flow out the bottom thereof along with the alcohol, free of water. As it flows downward through the upper zone of the column, it successively contacts the ascending vapors of aqueous alcohol and preferentially carries the alcohol downward. Moreover, a higher concentration of gasoline or its fraction is present throughout the lower zone of the dehydration drying column since it is flowing out of the base enhancing the volatility of water throughout the whole column and, consequently producing an anhydrous bottoms product which is gasohol, or a motor fuel blend with alcohol.

Figure 4:
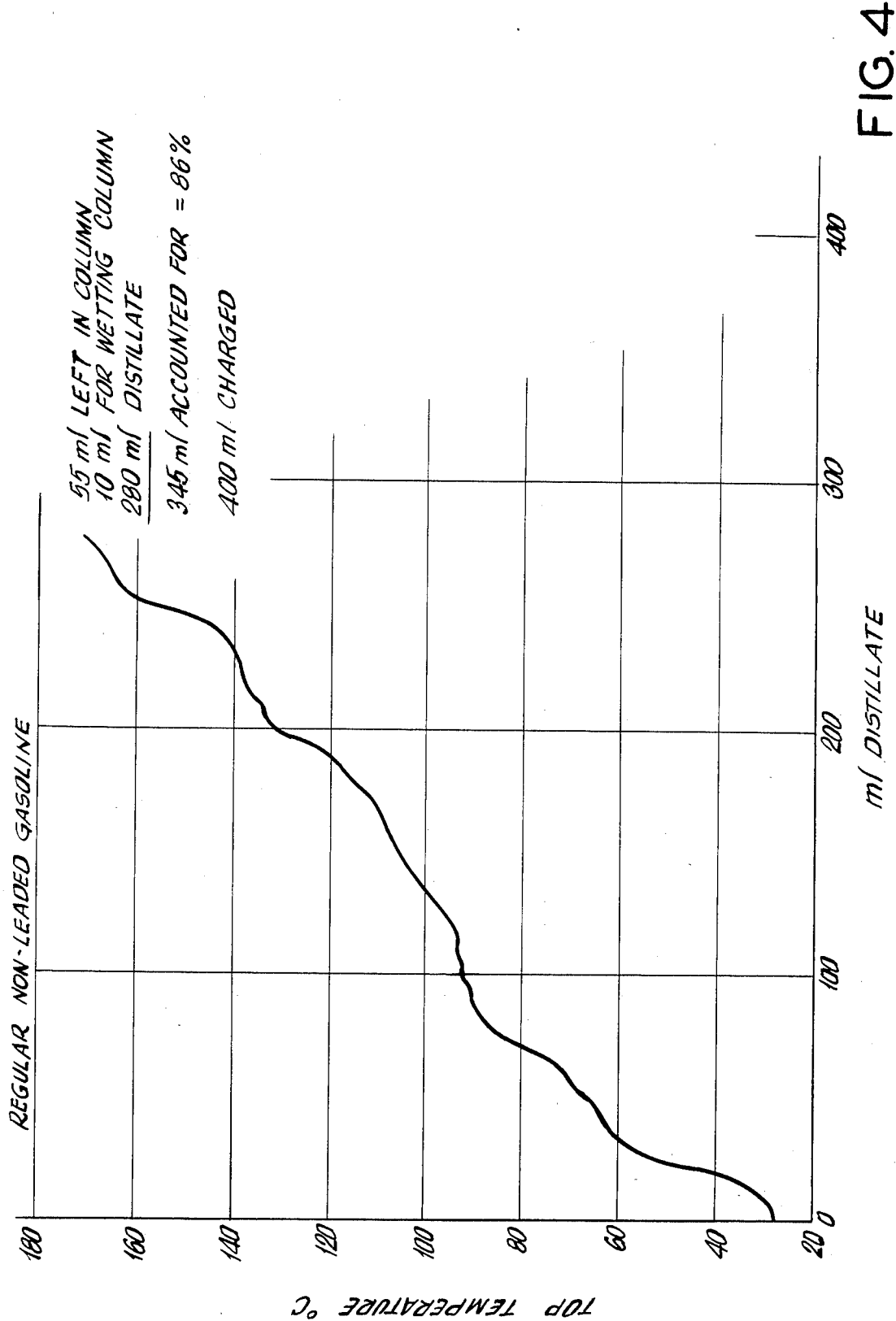
FIG. 4 is a flow sheet showing diagrammatically a typical boiling curve for non-leaded gasoline.

Though the bulk of the gasoline is in the $C_6$–$C_{12}$ range, boiling above 60° C., there is a front end in the distillate fraction of about 7% (see FIG. 4) $C_5$ fractions boiling from 27° C. to 60° C. and also a small amount of butane that boils at −0.5° C. Consequently, even though chilled water is used in the condenser (and 27° C. boiling material is readily condensed) the total recovery is only 86%, including the distillate obtained contents of the pot and allowance for any remaining on the packing. Operating as generally set forth above with the gasoline led to the top of the column in an amount of 6 to 9 times the alcohol feed rate, water is present as a separate liquid phase on many of the plates and by removing it by decantation from the renewal plates, as well as, of course, from the overhead reflux decanter, an anhydrous alcohol-gasoline fraction bottoms is readily obtained with quite reduced heat to the bottoms of the column. Although such described distillation procedure is particularly quite successful, its incorporation into a total process poses many problems. Accordingly, it is to be understood that it is within the scope of the improved process of this invention to encompass an entire plant to satisfacorily produce an alcohol for fuel from a fermented feed containing alcohol in the usual concentration of up to 12 volume % alcohol.

DESCRIPTION OF THE PREFERRED EMBODIMENTS

Turning more particularly to FIG. 1 a typical known process system for making motor fuel containing alcohol, that is gasohol, as illustrated there includes a dehydration drying column 1A and a stripper or recovery column 2A which is used to remove water from aqueous alcohol, the normal commercial alcohol generally containing 6% to 7% water by weight as manufactured, the anhydrous alcohol so formed subsequently being mixed with gasoline to form gasohol.

Column 1A which is divided into upper and lower zones is provided with a plurality of plates (not shown). The column is also provided with a lower outlet line 4A through which anhydrous alcohol, such as ethanol, is passed to a holding tank 5A. Another outlet line 6A is connected to the upper zone of the column 1A and to a decanting tank 7A into which liquid formed from vapors collected from the upper zone of the column are fed after being condensed by condenser 8A. Tank 7A is also provided with a return line 9 through which part of the liquid in tank 7A is returned to the upper zone of column 1A.

A balance tank 10A, which contains benzene, the entraining liquid, delivered to the tank from a source (not shown), is connected through line 11A, provided with pump 12A, to line 9A, thereby providing benzene to the upper zone of column 1A, and, as well, to the lower zone through line 13A. In addition, line 14A connects line 9A to balance tank 10A to provide liquid from tank 7A which has been collected from the upper zone of column 1A and mix the same with make-up benzene.

Tank 7A is also provided with line 15A connecting it with the upper zone of recovery or stripper column 2A which, like column 1A, is divided into upper and lower zones and provided with a plurality of plates (not shown) in the manner known to the art. An outlet line 16A is provided on the bottom of column 2A to remove separated water which may simply be discarded or led off for other uses. Heat to column 2A is provided by reboiler 17A or may be provided by direct injection of live steam from a suitable source (not shown). Overhead vapor from column 2A is carried by line 18A to condenser 19A to provide the reflux for the top of column 2A and net product of the benzene and alcohol removed from the water led to the column by line 15A and recycled to the drying column 1A through line 20A.

Gasoline from a suitable source (not shown) is stored in tank 21A and mixed with anhydrous alcohol from tank 5A in the desired ratio in line 22A to provide a gasohol product which is led off to storage for future use, the alcohol being led from tank 5A to line 22A by way of line 23A. It is to be noted that in this arrangement the initial incoming aqueous alcohol is led into the upper zone of column 1A by means of line 24A from a suitable source (not shown).

As previously mentioned, benzene is a useful entrainer, although other suitable materials that will form a ternary azeotrope with aqueous alcohol when such materials are brought together and form two liquid phases when condensed can likewise be employed. In operation, the upper zone of column 1A gives an overhead vapor rich in the ternary azeotrope which is condensed in condenser 8A, the condensate then being led to decanting tank 7A where the two liquid phases are separated, the upper phase consisting of benzene and alcohol with a minor amount of water. The benzene layer is returned to the drying column as reflux and the water layer is led to the recovery or stripper column 2A where water is eliminated as bottoms and the organic portion (benzene and alcohol) low in water is led overhead and recycled to the upper zone of the drying column 1A.

In order for the drying column to provide an anhydrous bottom alcohol product, there must be a considerable concentration of entrainer such as benzene on the plates in the lower zone of the column below the point at which incoming aqueous alcohol fuel is introduced into the column. This is accomplished by adding benzene or benzene rich phase from the balance tank to the column in the reflux or at other points until the bottoms are dry and then removing a sufficient amount of the layer from the decanter tank or from the reflux line to the balance tank until the bottoms are just free of benzene. If the column is not loaded with benzene through the upper zone and sufficient inventory built up to have benzene in the lower zone as well, the preferential bottoms product will be water or aqueous alcohol, no matter how much boil-up or how many plates are used in the column. Thus, it is seen that the typical known system for making gasohol is not only relatively complex but must also be delicately balanced in order to provide anhydrous alcohol which must then be subsequently mixed with gasoline to provide the final gasohol product. Moreover the alcohol is under close government control, must be denatured in an agent's presence, and lastly, chemicals added.

Figure 2:
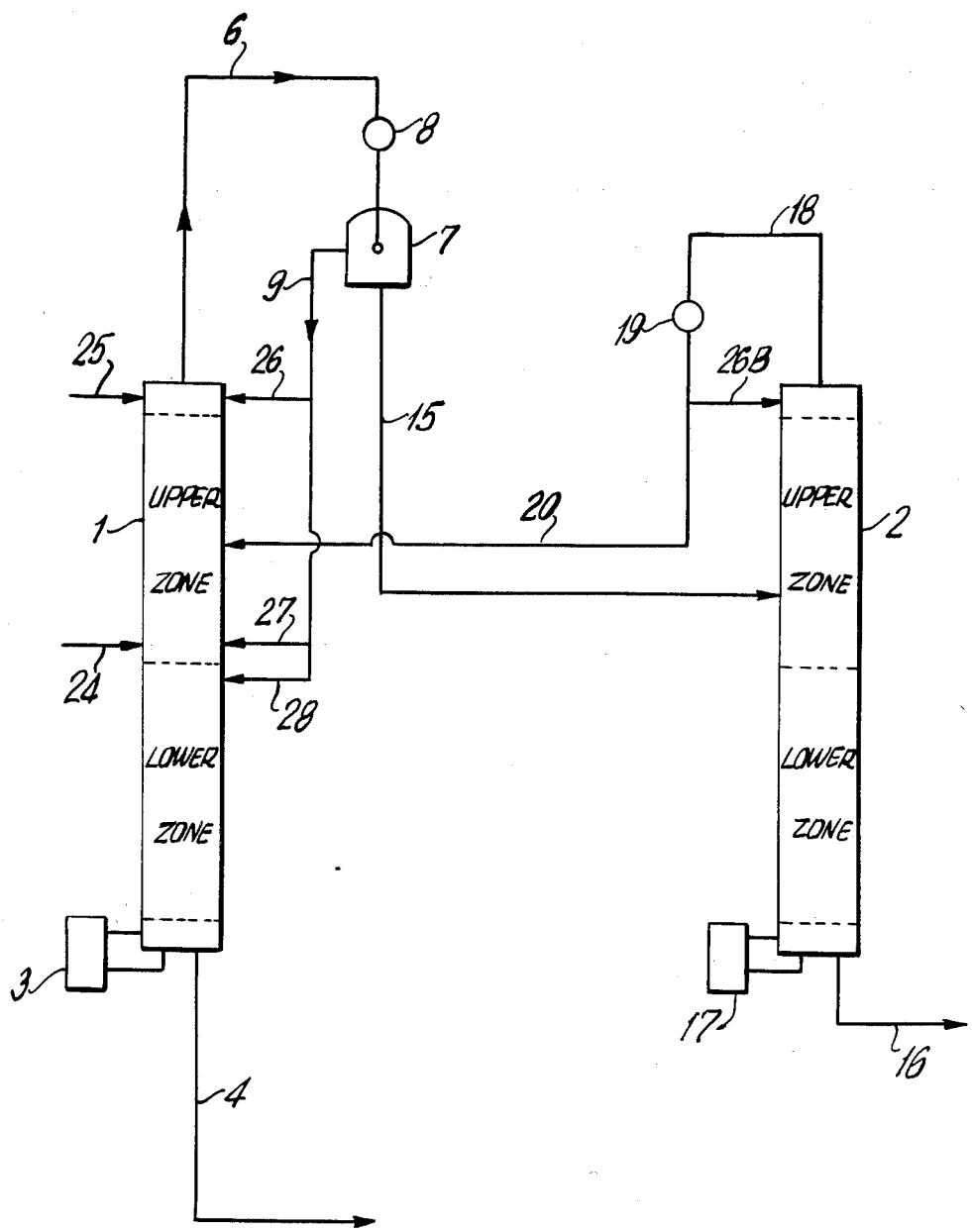

In contrast, in accordance with the present invention, the process illustrated in FIG. 2 is not only simplified but avoids the necessity of a separate dehydration of aqueous alcohol and subsequent mixing thereof with gasoline to provide the final desired product. Turning to the illustration of FIG. 2, it is to be noted that the detailed balancing system employed in the system of FIG. 1 is eliminated.

In the system shown in FIG. 2, the dehydration drying column 1 is the same as that of FIG. 1 except that it is provided in the upper zone with an additional inlet line 25 located near the top of the upper zone to provide for the introduction to the column of gasoline or a gasoline fraction which is employed as the entrainer and extractant in the ratio of about 9 to 1 to the incoming aqueous alcohol which is introduced through line 24 as in the previous systems. On the other hand, product motor fuel containing alcohol from which water has been removed is collected directly from the bottom of column 1 by way of line 4 and led to storage for future direct use as gasohol.

The process of this invention is accomplished by the system arrangement of FIG. 2 in the following manner.

Aqueous alcohol either in vapor or liquid form, such as commercial ethanol containing 6% to 7% water by weight, is introduced into column 1 by way of line 24. As is well understood to workers in the art, the portion of the column above the feed point or plate is defined as the upper zone of the column and and that below the feed point or plate as the lower zone. Gasoline or a gasoline fraction which is employed as the entrainer and extractant is introduced to the upper zone of the column through line 25 forming a ternary azeotrope with the aqueous alcohol and the column is heated by reboiler 3. As the gasoline or gasoline fraction moves downward, as previously mentioned, it successively contacts the ascending vapors of the aqueous alcohol and preferentially moves the alcohol downward also, both the gasoline or its fraction and alcohol moving downward into the lower zone of the column and through line 4 to storage as product motor fuel, that is gasohol, gasoline containing alcohol, or as an alcohol rich blending fraction which are substantially completely water free.

In the meantime, rising vapors which consist of water, gasoline or its fraction and alcohol are collected at the top of column 1 as overhead vapors and led by way of line 6 to tank 7 passing through condenser 8 where they are condensed. In tank 7, the condensate is separated as by decantation into two liquid phases or layers, the upper layer being principally gasoline containing alcohol and a minor amount of water and lower layer being alcohol and water containing a minor amount of gasoline.

The gasoline layer is recycled through line 9 to column 1 being added to the top plate generally when producing a 90%–10% to 70%–30% gasoline-alcohol product, but being added in part to the upper zone or lower zone in the vicinity of the feed 24 when producing products containing only 10 to 20% gasoline and a gasoline fraction is being used as the dehydrating medium.

On the other hand, the water phase or layer containing alcohol and a minor amount of gasoline in tank 7 is led by way of line 15 to the upper zone of recovery or stripping column 2 which is similar in design to the column of FIG. 1. Column 2 is heated by reboiler 17 or by direct injection of live steam to a temperature sufficient to vaporize the gasoline and alcohol which are collected as overhead vapors and led through line 18 to condenser 19 where condensation takes place, part of the condensate being then led through line 20 back to the upper zone of column 1 at a point on the column above the point of introduction of the aqueous alcohol to the column and the remainder being recycled to the upper zone of the stripping column, preferably at the top plate, through line 26B. In the meantime, water flows downwardly from the upper zone of the stripping column into the lower zone and is discharged as bottoms by way of line 16 either to discard or other use.

The presence of butane and other quite low boiling components in the gasoline, however, give rise to a low top temperature in line 6 and subsequent loss of these light ends from the system. In an alcohol manufacturing plant one generally desires to make a more nearly alcohol product and not use the large excess of gasoline.

Figure 3:
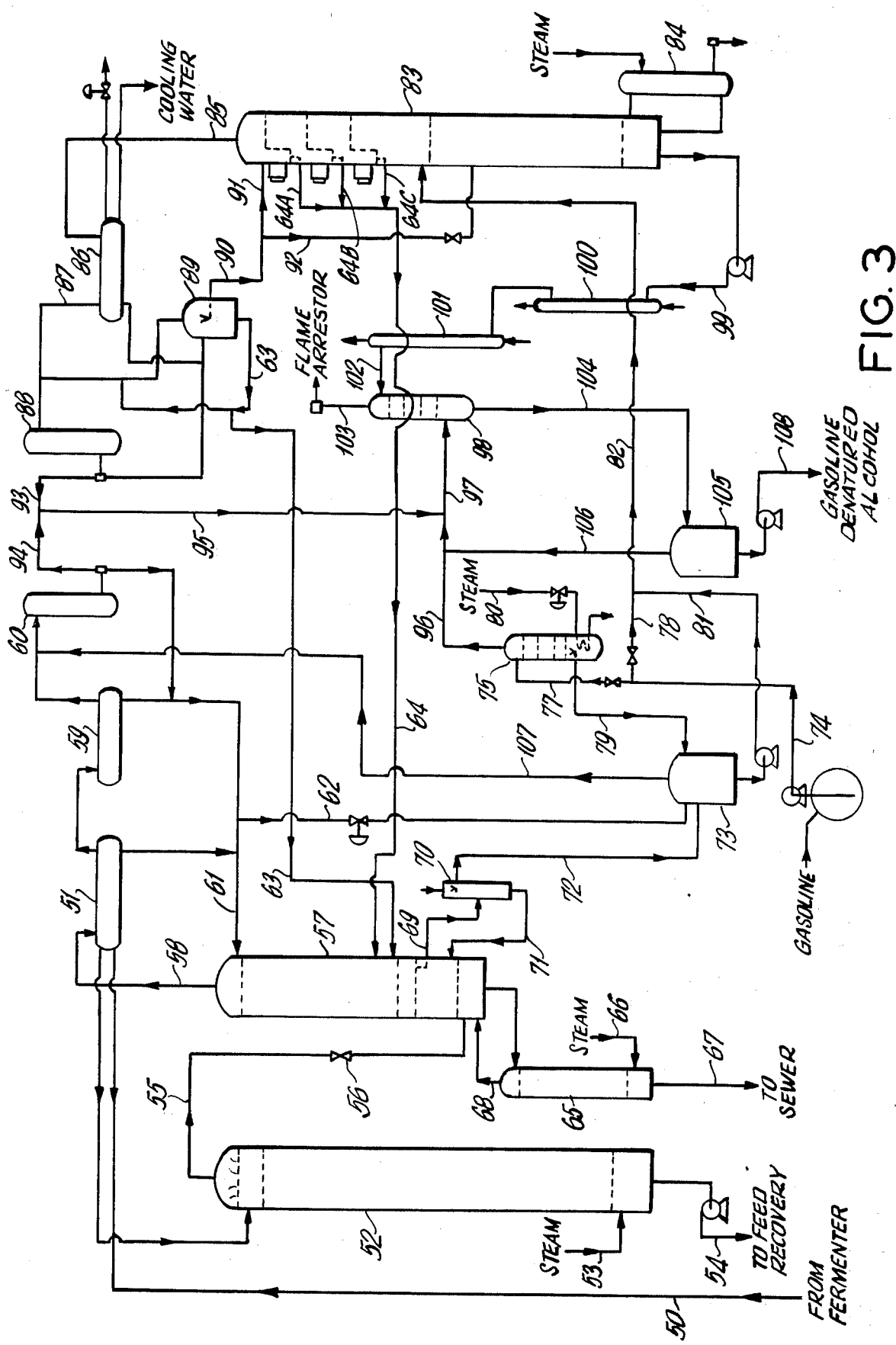
FIG. 3 is a flow sheet showing diagrammatically a complete system arrangement for making anhydrous alcohol completely denatured with gasoline employing the denaturing gasoline as the entrainer-extractant.

Turning next to FIG. 3, there is shown there the more detailed and desired embodiments of the invention for accomplishing the end result.

The unit shown in FIG. 3 generally comprises a beer stripper 52 with about 24 stripping plates (not shown) as known in the art below the feed, an average of 18 to 20 plates being common in the art, and a single foam disengaging plate above the feed with no reflux being returned and being preheated to at least on the order of 155° F. (69° C.) if preheated by exchange with overhead vapor only, but desirably to 170° F. (77° C.) or higher, if preheated by exchange with the beer still bottoms or other available recoverable source of heat. The unit also includes a beer rectifier 57 with 24 to 42 rectifying plates (not shown) which takes vapor from the beer stripper and the vapor from a 15–22 plate water stripper 65 which is heated by a small amount of direct steam and has as net bottoms only the amount of water in the vapor from the beer stripper, the overhead of the beer rectifyer being condensed by preheating the beer feed. The unit further includes a condenser 59 and/or other means with sufficient reflux returned to give usually a 190 to 191.5 proof product (though in some cases only about 185 proof); and a drying column 83 of about 50 plates (although as few as 20 to 25 are operative, though with increased heat use) heated at the base with a reboiler 84, provided with a condenser 86 at the top, a decanter 89 for the reflux, and decanting plates designed for separation of water at various zones in the column 83 in amounts of up to about 40% of the amount of water layer removed from the decanting plates. The top temperature of the drying column 83 is controlled by varying the amount of water provided to the main condenser 86, more water giving a lower top temperature and less water a higher top temperature. The uncondensed low boilers from the drying column condenser 86 and/or the low boilers from a gasoline feed heater 75 are passed into the bottom of a vent scrubber 98 to the top of which the drying column bottoms alcohol-gasoline product, cooled to a temperature in the order of about 50° F. (10° C.) by cooler 100 and subcooler 101, is fed. The water layer containing gasoline and alcohol that is removed from the drying column overhead decanter 89 and the special decanter plates is fed to the beer rectifyer 57 where the beer stripper vapor is used to concentrate the alcohol from the fermented feed and to recover the dissolved gasoline. The gasoline is fed to the gasoline heater 75 for elimination of butane then mixed with the alcohol-gasoline beer rectifyer overhead product for feeding into the drying column.

Operating the system on a pilot plant scale in an alcohol plant indicates the desirability of producing a gasoline denatured alcohol instead of the conventional gasohol containing 10% alcohol. Such operation gave, for example, the following results employing regular nonleaded gasoline and anhydrous alcohol vapor feeds. Alcohol to gasoline ratio was increased desirably to give up to 85% to 90% alcohol. The initial experimental runs were conducted with the anhydrous alcohol vapor feed and addition of the gasoline to the top of a vertical condenser, thereby scrubbing the overhead vapor to help retain the light ends and enhance the separation in the overhead decanter. At a 10% to 12% gasoline product the top temperature of the drying column was 28° C. to 30° C. and water layers were present on about the top 10 trays. The trays yielded about 40% of the total water layer. The product had a water content generally less than about 0.01% but the material balance did not close, indicating appreciable loss of light ends in the vapor which passed out of the column and in the water layer which was discarded. Runs with gasoline to the top plate of the drying column gave an overhead temperature of 50° C. and a recycled water layer of 20% water with about 20% coming from the top decanting trays of the drying column. The alcohol-gasoline product at 60% alcohol had about 0.1 weight % water. With a liquid alcohol feed, top temperature was 36° C., water content in the recycle was 30%, about 30% from the top 8 trays. The water layer from the trays removed the slight yellow color from the nonleaded gas employed and a very heavy oily waxy material was present in the water taken out of the water recovery column as bottoms, even though base temperature was just over 100° C. It was apparent, however, that in the presence of whole gasoline the drying column worked well where one took advantage of removing water by decantation from the plates instead of using a considerable amount of added heat to drive it all overhead and the essentially non-volatile components at 100° C. in the gasoline are added below the plates which separate out the water. As top temperature varied, so did the percentage of water in the recycle water layer and the proportion of water removed by decantation from the trays. At 55% alcohol-gasoline product with about 0.1 weight % water and at a top temperature of 30° C., recycle water was about 40+% water with about 25% of it from the top 8 trays. The gasoline layer from the decanter contained about 0.1 weight % water and 4 to 6 weight % alcohol. At 85% alcohol product with a top temperature of 35° C., water was nearly 40%; 30% at 50° C. top temperature, 19% at 60° C. top temperature and 10% at 74° C. top temperature with no side water being produced. Above about 65° C. top temperature, when the alcohol was over about 70% in the bottoms the water in the alcohol-gasoline product increased to about 1.5 weight % at the 74° C. top temperature. Above about 80% alcohol in the bottoms, without chilled vent condensers, it was difficult to produce a product down to 0.1 weight % water due to the loss of the small amount of effective entraining fraction. Best results were obtained with about a 50° C. temperature and with some gasoline layer from decanter being recycled below the feed plate of the drying column. Only by adding a scrubber to the gas from the vent condenser and using the alcohol-gasoline product chilled to about 50° F. (10° C.) as scrubbing medium was the total material balance throughout the unit able to be closed. Since the butane and light ends are dissolved in the gasoline at normal temperatures 70° F.–80° F. (21° C.–27° C.) it is easy to redissolve them in the alcohol-gasoline product by scrubbing them from the vent condenser vents.

It is to be noted that the water layer recycle to the beer rectifier 57 contains an appreciable quantity of gasoline fractions and all of the alcohol stripped from the beer feed is contaminated in the beer rectifyer. It is thus impossible to withdraw from the system any alcohol which is not contaminated with gasoline. Therefore, only gasoline contaminated alcohol can be withdrawn from the system and such is indicated by the odor of the product. On the other hand, a non-return valve in the vapor line from the beer stripper to the beer rectifyer makes it impossible for any gasoline, vapors or otherwise, to get into the beer stripper and contaminate the by-product feed.

Gasoline obtained from 3 different service stations and sold as regular non-leaded gasoline as well as a reformate, and a platformate fraction obtained directly from a fraction refinery were used in various runs in the described system. Debutanized gasoline gave less overhead gasoline layer reflux than whole gasoline.

A more detailed description of the complete system illustrated in FIG. 3 and the operation thereof follows. Fermented material containing usually 11 to 12 volume % alcohol (though as low as 2.5% alcohol from fermented whey, for example, may be used) is introduced by way of line 50 through the preheater 51 and into the beer stripper 52. Direct steam or vapor is added to the beer stripper by line 53 to strip the alcohol from the overflowing feed and give an alcohol free bottoms product at 54. The overhead vapor in line 55 containing about 20 to 50 weight % alcohol flows through non-return valve 56 and into the beer rectifier 57. The overhead vapor in line 58 containing the alcohol from the fermenter in addition to the alcohol and gasoline dissolved in water layers fed into rectifier 57 through lines 63 and 64 is partially condensed in feed heater 51 and condenser 59, then finally, to the extend possible, with coldest cooling water in vent condenser 60. Condensed liquid from these condensers is returned through line 61 as reflux with product being taken off through line 62 by temperature control for alcohol concentration into surge tank 73. If the fermented feed contains fusel oil it may be removed at line 69, separated in fusel oil separator 70 with the layer being returned through line 71 and any oil product drawn off through line 72 to surge tank 73. The bottoms from beer rectifier 57 are fed into water stripper 65, stripped by steam from line 66, and withdrawn free of alcohol through line 67 for discard. The vapor from water stripper 65 flows through line 68 into the back of the beer rectifier.

Gasoline is fed in the desired ratio to the alcohol content of the fermented feed through line 74 into gasoline heater 75 by line 77 where steam at line 80 may be added to control temperature flowing out of line 79 into surge tank 73. The alcohol gasoline mixture is fed by line 81 into line 82 where it may be joined by all or a portion of the gasoline from line 74 directly without heating for feed into the drying column 83. The reboiler 84 supplies heat to the base and the overhead vapors pass through line 85 into condenser 86. The temperature in line 87 is maintained by controlling cooling water to condenser 86 and vent condenser 88 is used to condense such material as may be readily condensed with coldest cooling water. Reflux from the condenser 88 is fed into decanter 89 where the gasoline layer in line 90 is fed through line 91 as reflux to the top of column 83 or partially by line 92 to a lower plate of the column. Water from the decanter is fed by line 63 to the beer rectifier 57 and also the water layers decanted on the top several trays at lines 64A, 64B and 64C, etc. through line 64. The anhydrous alcohol bottoms is removed through line 99, cooled in cooler 100, chilled or subcooled with such cooled water in chiller 101, then fed to the top of vent scrubber 98. The butanes and other low boilers not readily condensible in the vent condensers flow through lines 93 and 94 into line 95 being joined with vapors from the gasoline feed heater through line 96 and product tank vent line 106 to flow through line 97 into vent scrubber 98. Here the descending chilled alcohol-gasoline product dissolves any condensibles permitting only non condensible to flow out line 103 through a flame arrestor. The alcohol-gasoline product containing all light ends flows through line 104 into product tank 105 for later transfer to storage or use through line 108.

It is to be understood that while the process of this invention is particularly useful in making alcohol blending fraction for motor fuel containing ethanol, the term alcohol as employed throughout this specification and in the appended claims is to be understood to include other alcohols or similar oxygenated organic compounds also such as, for example, but not limited to, propanol, butanol, pentanol and the like and, as well, their isomeric forms or any commercial denatured formula for ethanol.

The process of this invention can be carried out under widely varying conditions of pressure and temperature. In general, the process is carried out under conditions of positive pressure. It is to be understood in this respect that the most efficacious pressure conditions to be employed in carrying out the process of this invention will be, in the main, dependent upon the particular boiling points of the gasoline or gasoline fraction being used.

It is to be understood that it is within the purview of this invention to carry out the process thereof when employing a mixture of alcohols either as liquid or vapor feedstock and, as well, to provide a final gasohol product which can vary widely in the amounts of gasoline and alcohol present in the final product.

It is to be understood, therefore, that the descriptive embodiments of this invention as set forth herein are illustrative only and the concept of this invention is not to be limited thereby, except as defined in the appended claims.

What is claimed is:

1. A process for making an anhydrous fraction from a fermented feed material or beer comprising contacting said fermented feed material or beer directly with steam vapor volatilizing the alcohol in said feed or beer and producing an alcohol free bottoms, conducting said alcohol vapor through a one-way flow mechanism into a column provided with a plurality of trays located one above the other, refluxing said alcohol vapor over said plurality of trays and concentrating said alcohol vapor to high-proof alcohol, utilizing the reflux and vapor to concentrate additional alcohol from a dilute aqueous gasoline-containing recycle and contacting said net total water bottoms from the concentration step with direct steam prior to discharge to sewer, feeding said concentrated alcohol with recovered gasoline from said recycle as contaminant along with additional gasoline, optinally heated to eliminate light ends, into a drying column, heating the alcohol gasoline feed with heat from a reboiler and vaporizing overhead the azeotropic fractions containing alcohol, gasoline and water, condensing said azeotropic fractions and forming two liquid phases, returning the gasoline phase as reflux to said drying column, recycling the water phase as initiator prior to the alcohol concentrating column, cooling and subcooling the anhydrous alcohol-gasoline bottoms, contacting countercurrently the low boiling components vented from the various condensing operations and gasoline heater and producing a final product which is completely denatured alcohol ready for removal from premises and containing the entire component of the originally added gasoline.

2. A process according to claim 1 wherein the gasoline used as an entrainer is heated to a predetermined temperature to remove light ends fractions before introduction thereof into the drying column.

3. A process according to claim 1 including recycling the gasoline layer to the dehydration drying column at a point above the point of introduction of the aqueous alcohol to said column.

4. A process according to claim 1 including recycling a portion of the gasoline layer to the dehydration drying column at a point below the point of introduction of the aqueous alcohol.

5. A process according to claim 1, wherein the hydrocarbon introduced to the dehydration drying column is a fraction of gasoline.

6. A process according to claim 1 including introducing the condensate water layer into a stripping column, stripping the gasoline and alcohol therefrom as overhead and condensing the same, refluxing at least part of said condensate back to the stripping column and recovering water from the bottom of said stripping column while recycling the remainder of said condensate to the dehydration drying column.

7. A process according to claim 1 including separating by decantation the condensate into a layer of gasoline and alcohol containing a minor amount of water and a layer of water and alcohol containing a minor amount of gasoline.

8. A process according to claim 1, wherein the alcohol is ethanol.

9. A process according to claim 1, wherein the alcohol is a commercial denatured ethanol.

10. A process according to claim 1 wherein the top several trays of the drying column are so designed to separate a water layer phase from the gasoline reflux and removed from said trays as said water layer phase is formed.

11. A process according to claim 1 wherein the water layers with dissolved gasoline removed from the dehydration of the alcohol are reconcentrated by utilizing the stripping vapor from initial recovery of alcohol from a fermented material, said vapor line being fitted with a non-return valve to insure no contamination of fermented stock and said dissolved gasoline contaminating the entire recovery column product said net water being stripped for disposal with independent stripping trays and no return whatsoever, liquid or vapor, to the fermented stock stripper.

12. A process according to claim 1 including separating and removing a water phase as it is formed from the gasoline reflux on the top several trays of the drying column.

13. A process according to claim 11 including recycling the gasoline condensate layer to the dehydration drying column.

* * * * *